(12) United States Patent
MacDonald et al.

(10) Patent No.: US 8,287,461 B2
(45) Date of Patent: Oct. 16, 2012

(54) VEIN IDENTIFICATION TECHNIQUE

(75) Inventors: John Gavin MacDonald, Decatur, GA (US); Kaiyuan Yang, Cumming, GA (US); Jaeho Kim, Roswell, GA (US); JungMo Kim, GyeongGi-do (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1101 days.

(21) Appl. No.: 11/939,082

(22) Filed: Nov. 13, 2007

(65) Prior Publication Data

US 2009/0124925 A1    May 14, 2009

(51) Int. Cl.
*A61B 5/00*    (2006.01)

(52) U.S. Cl. ........................................... 600/549

(58) Field of Classification Search ................... 604/116; 374/141; 600/549
See application file for complete search history.

(56) References Cited

U.S. PATENT DOCUMENTS

| | | | |
|---|---|---|---|
| 3,998,210 A * | 12/1976 | Nosari ............................ | 600/549 |
| 4,015,591 A | 4/1977 | Suzuki et al. | |
| 4,100,324 A | 7/1978 | Anderson et al. | |
| 4,144,370 A | 3/1979 | Boulton | |
| 4,175,543 A * | 11/1979 | Suzuki et al. ................... | 600/549 |
| 4,378,808 A * | 4/1983 | Lichtenstein .................. | 600/549 |
| 4,448,204 A | 5/1984 | Lichtenstein | |
| 4,620,941 A | 11/1986 | Yoshikawa et al. | |
| 4,957,949 A | 9/1990 | Kamada et al. | |
| 4,971,068 A | 11/1990 | Sahi | |
| 5,281,570 A | 1/1994 | Hasegawa et al. | |
| 5,350,624 A | 9/1994 | Georger et al. | |
| 5,350,634 A | 9/1994 | Sumii et al. | |
| 5,431,697 A | 7/1995 | Kamata et al. | |
| 5,500,040 A * | 3/1996 | Fujinami ......................... | 522/53 |
| 5,527,385 A | 6/1996 | Sumii et al. | |
| 5,681,380 A | 10/1997 | Nohr et al. | |
| 5,785,179 A | 7/1998 | Buczwinski et al. | |
| 5,964,351 A | 10/1999 | Zander | |
| 6,030,331 A | 2/2000 | Zander | |
| 6,158,614 A | 12/2000 | Haines et al. | |
| 6,269,969 B1 | 8/2001 | Huang et al. | |
| 6,269,970 B1 | 8/2001 | Huang et al. | |
| 6,273,359 B1 | 8/2001 | Newman et al. | |
| 6,315,864 B2 | 11/2001 | Anderson et al. | |

(Continued)

FOREIGN PATENT DOCUMENTS

WO    WO 0114149 A1    2/2001

OTHER PUBLICATIONS

Cost, Frank. "The Pocket Guide to Digital Printing." Delmar Publishers: Albany, New York, 1997: p. 145.
CIE No. 15.2—Colorimetry, 1986, 74 pages with Appendix.
ISO 7724/1 Paints and Varnishes—Colorimetry—Part 1: Principles, International Organization of Standards, 1984.

(Continued)

*Primary Examiner* — Nicholas Lucchesi
*Assistant Examiner* — Diva K Chander
(74) *Attorney, Agent, or Firm* — Dority & Manning, P.A.

(57) ABSTRACT

A technique for identifying a vein in a patient is disclosed. The technique involves the application of a thermochromic ink to a venous area on the skin of a patient (e.g., human or animal). The thermochromic ink comprises thermosensitive color-changing microcapsules that contain a proton-accepting chromogen and a desensitizer. The desensitizer possesses a melting point above which the chromogen is capable of becoming protonated, thereby resulting in a color change. Thereafter, the venous area is observed for the color change.

22 Claims, 1 Drawing Sheet

U.S. PATENT DOCUMENTS

| | | | |
|---|---|---|---|
| 6,328,910 | B1 | 12/2001 | Askill et al. |
| 6,464,646 | B1 | 10/2002 | Shalom et al. |
| 6,863,720 | B2 | 3/2005 | Kitagawa et al. |
| 7,297,143 | B2 * | 11/2007 | Woloszko et al. .............. 606/41 |
| 2004/0186469 | A1 * | 9/2004 | Woloszko et al. .............. 606/41 |
| 2007/0252115 | A1 * | 11/2007 | Arehart et al. ................ 252/583 |
| 2007/0255189 | A1 * | 11/2007 | Halanski et al. .................. 602/8 |
| 2007/0260229 | A1 | 11/2007 | Navarro et al. |
| 2009/0046760 | A1 * | 2/2009 | Matheson .................... 374/141 |

OTHER PUBLICATIONS

ASTM E 1164-02, Standard Practice for Obtaining Spectrometric Data for Object-Color Evaluation, American Society of Tool and Manufacturing Engineering, 2002.

Product Information Sheet on Chromicolor® AQ Ink/ Photopia® AQ Ink/ Aroma AQ Ink from Matsui International Co. Inc., 4 pages.

Search Report and Written Opinion for PCT/IB2008/053706 dated May 25, 2009, 14 pages.

* cited by examiner

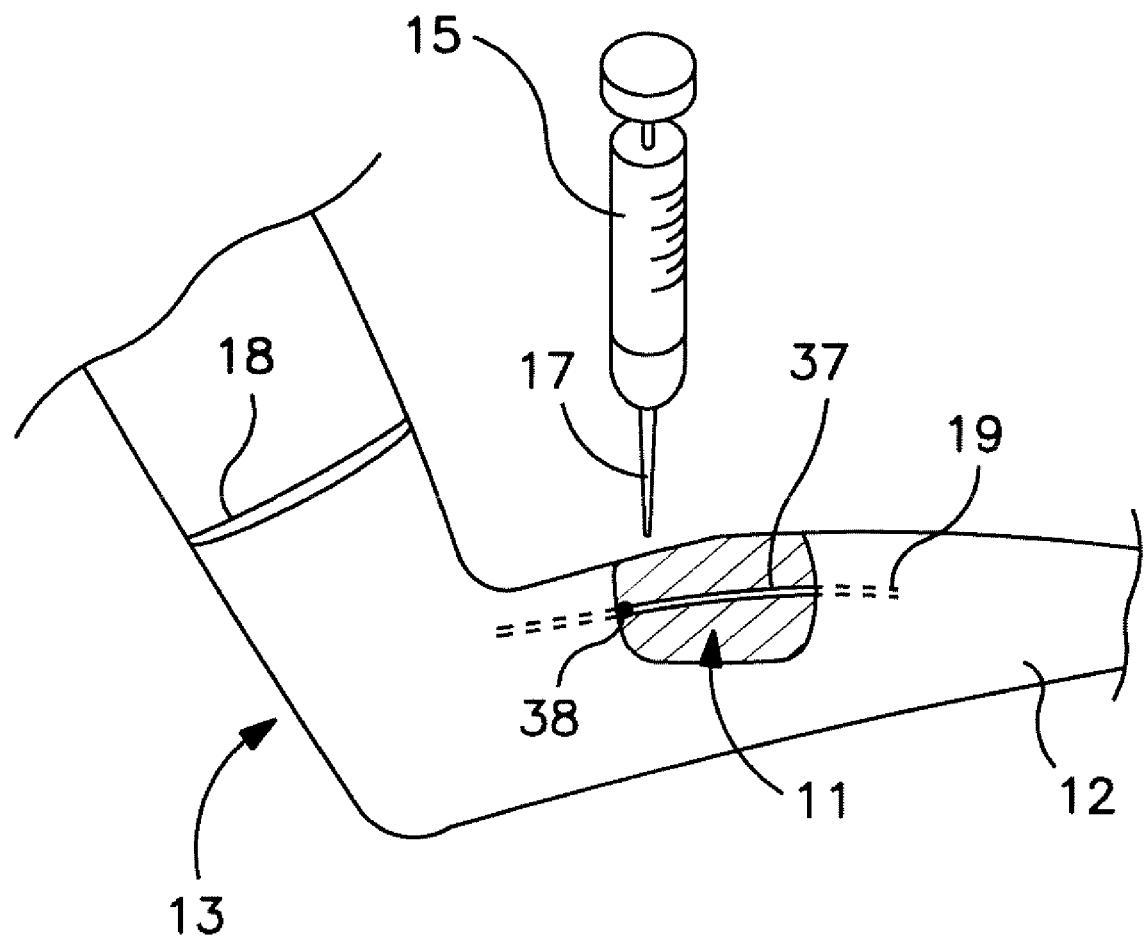

VEIN IDENTIFICATION TECHNIQUE

BACKGROUND OF THE INVENTION

One of the most common medical tests or procedures performed on patients is associated with the analysis of the blood of the patient or the infusion of fluid into the patient. Usually the first step in such a test procedure involves obtaining a sample of blood by invasive techniques. Of course, to puncture the vein of the patient, the vein must first be located. The location of the vein is not particularly difficult if it can be visually seen or felt. To enhance the probability of visual sighting or feeling, an elastic strap is often tightly wound around the upper arm of the patient. This produces a differential in the pressure of the blood being conducted by the veins. The human body responds to such a pressure differential by enlarging the veins in an attempt to provide a conduction path of less resistance. The enlarging of the veins makes them more prominent and therefore increases the probability that one of the veins can be located by viewing or feeling the arm of the patient. Unfortunately, the procedure for enlarging the veins is not always successful. For instance, because the vein is generally dark in color, it is even more difficult to sight a vein in the arm of a person having a dark colored pigment in his skin. Other characteristics of the patient that make it particularly difficult to sight or feel a vein are associated with small children, obesity, and old age. These characteristics generally mean that the vein is significantly recessed from the skin and therefore particularly difficult to visually sight or feel.

Various techniques have thus been developed to aid in the identification of veins. One such technique relies upon the fact that the temperature of the skin in proximity to a vein is generally greater than the temperature of the remaining portions of the skin. To detect the higher temperatures of the skin adjacent to the vein, liquid crystal materials have been employed that undergo a color change at the desired temperature. To improve color contrast, the liquid crystals are commonly applied to and viewed against a black background that serves to absorb the transmitted light. U.S. Pat. No. 3,998,210 to Nosari, for example, describes the use of encapsulated liquid crystals in a laminated article that includes a black background for locating veins in the body. Still another technique for enhancing the color contrast is described in U.S. Pat. No. 4,175,543 to Suzuki, et al., which involves cooling the skin with a cold pack before or after application of microencapsulated liquid crystals to produce a greater temperature gradient between the skin surface directly over the vein and adjacent areas of the skin. This temperature gradient is said to provide a sharper delineation of the vein for identification. One problem with the conventional vein identification methods, however, is that the liquid crystals employed generally have a low color density, poor color selectivity and are expensive. Further, the methods involved are too complex in that they often involve multiple steps to be performed by the user, such as color contrast, cooling, and so forth.

As such, a need currently exists for a simple, efficient, and effective method for rapidly identifying the presence of a vein.

SUMMARY OF THE INVENTION

In accordance with one embodiment of the present invention, a method for identifying a vein in a patient (e.g., human or animal) is disclosed. The method comprises applying a thermochromic ink to a venous area on the skin of a patient. The thermochromic ink comprises thermosensitive color-changing microcapsules that contain a proton-accepting chromogen and a desensitizer. The desensitizer possesses a melting point above which the chromogen is capable of becoming protonated, thereby resulting in a color change. Thereafter, the venous area is observed for the color change. In still another embodiment, a kit for puncturing the vein of a patient is disclosed that comprises a thermochromic ink capable of locating the vein through a change in color and a syringe associated with a needle for puncturing the vein located by the thermochromic ink.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which:

FIG. 1 illustrates the arm of a patient and an exemplary method for taking a blood sample from the arm using the thermochromic ink of the present invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a technique for identifying the location of a superficial vein (e.g., near the skin) in the human body. More specifically, a thermochromic ink is applied to a venous area of the body that contains thermosensitive color-changing microcapsules. The microcapsules include a proton-accepting chromogen. In solution, the protonated form of the chromogen predominates at acidic pH levels (e.g., pH of about 4 or less). When the solution is made more alkaline through protonation, however, a color change occurs. One particularly suitable class of proton-accepting chromogens are leuco dyes, such as phthalides; phthalanes; acyl-leucomethylene compounds; fluoranes; spiropyranes; cumarins; and so forth. Exemplary fluoranes include, for instance, 3,3'-dimethoxyfluorane, 3,6-dimethoxyfluorane, 3,6-di-butoxyfluorane, 3-chloro-6-phenylamino-flourane, 3-diethylamino-6-dimethylfluorane, 3-diethylamino-6-methyl-7-chlorofluorane, and 3-diethyl-7,8-benzofluorane, 3,3'-bis-(p-dimethyl-aminophenyl)-7-phenylaminofluorane, 3-diethylamino-6-methyl-7-phenylamino-fluorane, 3-diethylamino-7-phenyl-aminofluorane, and 2-anilino-3-methyl-6-diethylamino-fluorane. Likewise, exemplary phthalides include 3,3',3"-tris(p-dimethylamino-phenyl)phthalide, 3,3'-bis(p-dimethyl-aminophenyl)phthalide, 3,3-bis (p-diethylamino-phenyl)-6-dimethylamino-phthalide, 3-(4-diethylaminophenyl)-3-(1-ethyl-2-methylindol-3-yl)phthalide, and 3-(4-diethylamino-2-methyl)phenyl-3-(1,2-dimethylindol-3-yl)phthalide. Still other suitable chromogens are described in U.S. Pat. No. 4,620,941 to Yoshikawa, et al.; U.S. Pat. No. 5,281,570 to Hasegawa, et al.; U.S. Pat. No. 5,350,634 to Sumii, et al.; and U.S. Pat. No. 5,527,385 to Sumii, et al., which are incorporated herein in there entirety for all purposes.

A desensitizer is also employed in the thermosensitive color-changing microcapsules to facilitate protonation of the chromogen at the desired temperature. More specifically, at a temperature below the melting point of the desensitizer, the chromogen generally possesses a first color (e.g., white). When the desensitizer is heated to its melting temperature, the chromogen becomes protonated, thereby resulting in a shift of the absorption maxima of the chromogen towards either the red ("bathochromic shift") or blue end of the spectrum ("hypsochromic shift"). The nature of the color change depends on a variety of factors, including the type of proton-accepting chromogen utilized and the presence of any additional temperature-insensitive chromogens. The color change is typically reversible in that the chromogen deprotonates when cooled. Although any desensitizer may generally be employed in the present invention, it is typically desired that the desensitizer have a low volatility. For example, the desensitizer may have a boiling point of about 150° C. or higher, and in some embodiments, from about 170° C. to 280° C. Likewise, the melting temperature of the desensitizer is also typically from about 26° C. to about 34° C., and in some embodiments, from about 28° C. to about 33° C. Examples of suitable desensitizers may include saturated or unsaturated alcohols containing about 6 to 30 carbon atoms, such as octyl alcohol, dodecyl alcohol, lauryl alcohol, cetyl alcohol, myristyl alcohol, stearyl alcohol, behenyl alcohol, geraniol, etc.; esters of saturated or unsaturated alcohols containing about 6 to 30 carbon atoms, such as butyl stearate, lauryl laurate, lauryl stearate, stearyl laurate, methyl myristate, decyl myristate, lauryl myristate, butyl stearate, lauryl palmitate, decyl palmitate, palmitic acid glyceride, etc.; azomethines, such as benzylideneaniline, benzylidenelaurylamide, o-methoxybenzylidene laurylamine, benzylidene p-toluidine, p-cumylbenzylidene, etc.; amides, such as acetamide, stearamide, etc.; and so forth.

The color-changing microcapsules may also include a proton-donating agent (also referred to as a "color developer") to facilitate the reversibility of the color change. Such proton-donating agents may include, for instance, phenols, azoles, organic acids, esters of organic acids, and salts of organic acids. Exemplary phenols may include phenylphenol, bisphenol A, cresol, resorcinol, chlorolucinol, β-naphthol, 1,5-dihydroxynaphthalene, pyrocatechol, pyrogallol, trimer of p-chlorophenol-form aldehyde condensate, etc. Exemplary azoles may include benzotriaoles, such as 5-chlorobenzotriazole, 4-laurylaminosulfobenzotriazole, 5-butylbenzotriazole, dibenzotriazole, 2-oxybenzotriazole, 5-ethoxycarbonyl-benzotriazole, etc.; imidazoles, such as oxybenzimidazole, etc.; tetrazoles; and so forth. Exemplary organic acids may include aromatic carboxylic acids, such as salicylic acid, methylenebissalicylic acid, resorcylic acid, gallic acid, benzoic acid, p-oxybenzoic acid, pyromellitic acid, β-naphthoic acid, tannic acid, toluic acid, trimellitic acid, phthalic acid, terephthalic acid, anthranilic acid, etc.; aliphatic carboxylic acids, such as stearic acid, 1,2-hydroxystearic acid, tartaric acid, citric acid, oxalic acid, lauric acid, etc.; and so forth. Exemplary esters may include alkyl esters of aromatic carboxylic acids in which the alkyl moiety has 1 to 6 carbon atoms, such as butyl gallate, ethyl p-hydroxybenzoate, methyl salicylate, etc.

Encapsulation of the above-described components enhances the stability of the thermochromic ink during use. For example, the chromogen, desensitizer, developer, and other components may be mixed with a polymer resin (e.g., thermoset) according to any conventional method, such as interfacial polymerization, in-situ polymerization, etc. Suitable thermoset resins may include, for example, polyester resins, polyurethane resins, melamine resins, epoxy resins, diallyl phthalate resins, vinylester resins, and so forth. The resulting mixture may then be granulated and optionally coated with a hydrophilic macromolecular compound, such as alginic acid and salts thereof, carrageenan, pectin, gelatin and the like, semisynthetic macromolecular compounds such as methylcellulose, cationized starch, carboxymethylcellulose, carboxymethylated starch, vinyl polymers (e.g., polyvinyl alcohol), polyvinylpyrrolidone, polyacrylic acid, polyacrylamide, maleic acid copolymers, and so forth. The resulting microcapsules typically have a mean particle size of from about 5 nanometers to about 25 micrometers, in some embodiments from about 10 nanometers to about 10 micrometers, and in some embodiments, from about 50 nanometers to about 5 micrometers. Various other suitable encapsulation techniques are also described in U.S. Pat. No. 4,957,949 to Kamada, et al.; U.S. Pat. No. 5,431,697 to Kamata, et al.; and U.S. Pat. No. 6,863,720 to Kitagawa et al., which are incorporated herein in their entirety by reference thereto for all purposes. Commercially available encapsulated thermochromic substances may be obtained from Matsui Shikiso Chemical Co., Ltd. of Kyoto, Japan under the designation "Chromicolor" (e.g., Chromicolor AQ-Ink) or from Color Change Corporation of Streamwood, Ill. (e.g., black leuco powder having a transition of 33° C. or 41° C., red leuco powder having a transition of 28° C., yellow and red leuco powder having a transition of 31° C., or blue leuco powder having a transition of 33° C. or 36° C.).

The amount of the polymer resin(s) (e.g., thermoset) used to form the color-changing microcapsules may vary, but is typically from about 20 wt. % to about 80 wt. %, in some embodiments from about 30 wt. % to about 70 wt. %, and in some embodiments, from about 40 wt. % to about 60 wt. % of the microcapsules. The amount of the proton-accepting chromogen(s) employed may be from about 0.1 wt. % to about 20 wt. %, in some embodiments from about 0.5 wt. % to about 15 wt. %, and in some embodiments, from about 1 to about 10 wt. % of the microcapsules. The proton-donating agent(s) may constitute from about 0.5 to about 30 wt. %, in some embodiments from about 1 wt. % to about 20 wt. %, and in some embodiments, from about 2 wt. % to about 15 wt. % of the microcapsules. In addition, the desensitizer(s) may constitute from about 10 wt. % to about 70 wt. %, in some embodiments from about 15 wt. % to about 60 wt. %, and in some embodiments, from about 20 wt. % to about 50 wt. % of the microcapsules.

The nature and weight percentage of the components used in the thermosensitive color-changing microcapsules are generally selected so that the ink changes from one color to another color, from no color to a color, or from a color to no color at a desired activation temperature, which is generally from about 26° C. to about 34° C., and in some embodiments, from about 28° C. to about 33° C. in venous areas of the skin. However, the desired activation temperature may vary for different body parts. For example, the maximum skin temperatures normally observed over the veins in the antecubital fossa and upper forearm regions of the arm, the most frequent sites for venipuncture, are about 32° C. at the examining room temperature (approximately 21° C. to 25° C.). Alternate sites for venipuncture include additional regions of the upper extremities (e.g., hands, wrists, and remaining forearm regions), where the maximum skin temperatures over veins are normally about 30° C., and the lower extremities (e.g., the feet and legs), where the maximum skin temperatures over the veins are normally about 28° C. In light of the above, the activation temperature may be tailored to the desired body part. For example, the activation temperature may be from about 30° C. to about 34° C., and in some embodiments, from about 31° C. to about 33° C. for the antecubital fossa region; from about 28° C. to about 32° C., and in some embodiments, from about 29° C. to about 31° C. for the upper extremities, and from about 26° C. to about 30° C., and in some embodiments, from about 27° C. to about 29° C. for the lower extremities.

In some cases, it may be desirable to cool the skin over which the thermochromic ink is applied to produce a greater temperature gradient between the skin surface directly over a vein and adjacent areas of the skin. Namely, when the skin is cooled, rewarming occurs most rapidly over the veins due to the blood flow therein, which thus allows for enhanced delineation between the venous and non-venous areas. In this regard, a cooling agent may be employed in the thermochromic ink that is capable of vaporizing into the surrounding atmosphere and thus cool the skin through evaporative cooling. Any cooling agent may be employed that possesses an enthalpy of vaporization that is low enough to provide cooling to the skin. Generally speaking, the cooling agents have a latent heat of vaporization of about 45 kJ/mole or less, in some embodiments about 40 kJ/mole or less, and in some embodiments, from about 5 to about 39 kJ/mole.

One suitable class of cooling agents that may be employed include solvents, such as water; glycols (e.g., propylene glycol, butylene glycol, triethylene glycol, hexylene glycol, polyethylene glycols, ethoxydiglycol, and dipropyleneglycol); glycol ethers (e.g., methyl glycol ether, ethyl glycol ether, and isopropyl glycol ether); ethers (e.g., diethyl ether and tetrahydrofuran); alcohols (e.g., methanol, ethanol, n-propanol, iso-propanol, and butanol); triglycerides; ketones (e.g., acetone, methyl ethyl ketone, and methyl isobutyl ketone); esters (e.g., ethyl acetate, butyl acetate, diethylene glycol ether acetate, and methoxypropyl acetate); amides (e.g., dimethylformamide, dimethylacetamide, dimethylcaprylic/capric fatty acid amide and N-alkylpyrrolidones); nitriles (e.g., acetonitrile, propionitrile, butyronitrile and benzonitrile); sulfoxides or sulfones (e.g., dimethyl sulfoxide (DMSO) and sulfolane); and so forth. In addition to serving as a cooling agent, the solvent may also have other benefits, such as controlling the viscosity of the thermochromic ink and thus facilitating the formation of thin and uniform coatings on the skin. Certain solvents, such as organic solvents, may also have sanitizing and/or antimicrobial properties that can further reduce the risk of infection or contamination during venipuncture. For example, organic solvents, such as ethanol (enthalpy of vaporization of 38.6 kJ/mol) and methanol (enthalpy of vaporization of 37.4 kJ/mol), may be suitable cooling agents that also provide a sanitizing effect to the skin.

When employed, the total concentration of solvent(s) may vary, but is typically from about 30 wt. % to about 99 wt. %, in some embodiments from about 40 wt. % to about 95 wt. %, and in some embodiments, from about 50 wt. % to about 90 wt. % of the thermochromic ink. Likewise, the total concentration of the color changing microcapsules may range from about 1 wt. % to about 70 wt. %, in some embodiments from about 5 wt. % to about 60 wt. %, and in some embodiments, from about 10 wt. % to about 50 wt. %. Of course, the specific amount of solvent(s) employed depends in part on the desired solids content and/or viscosity of the thermochromic ink. For example, the solids content may range from about 0.01 wt. % to about 30 wt. %, in some embodiments from about 0.1 wt. % to about 25 wt. %, and in some embodiments, from about 0.5 wt. % to about 20 wt. %. By varying the solids content of the thermochromic ink, the presence of the color changing microcapsules may be controlled. For example, to form a thermochromic ink with a higher level of the microcapsules, the formulation may be provided with a relatively high solids content so that a greater percentage of the color-changing microcapsules are incorporated into the ink. In addition, the viscosity of the thermochromic ink may also vary depending on the application method and/or type of solvent employed. The viscosity is typically, however, from about 1 to about 200 Pascal-seconds, in some embodiments from about 5 to about 150 Pascal-seconds, and in some embodiments, from about 10 to about 100 Pascal-seconds, as measured with a Brookfield DV-1 viscometer using Spindle No. 18 operating at 12 rpm and 25° C. If desired, thickeners or other viscosity modifiers may be employed in the thermochromic ink to increase or decrease viscosity.

The thermochromic ink may also contain other components as is known in the art, such as a carrier (e.g., water) or co-carriers, such as lactam, N-methyl pyrrolidone, N-methylacetamide, N-methylmorpholine-N-oxide, N,N-dimethylacetamide, N-methyl formamide, propyleneglycol-monomethylether, tetramethylene sulfone, tripropyleneglycolmonomethylether, propylene glycol, and triethanolamine (TEA). Humectants may also be utilized, such as ethylene glycol; diethylene glycol; glycerine; polyethylene glycol 200, 300, 400, and 600; propane 1,3 diol; propylene-glycolmonomethyl ethers, such as Dowanol PM (Gallade Chemical Inc., Santa Ana, Calif.); polyhydric alcohols; or combinations thereof. Further, additional temperature-insensitive chromogens may also be employed to help control the color that is observed during use of the thermochromic ink. Other additives may also be included to improve ink performance, such as a chelating agent to sequester metal ions that could become involved in chemical reactions over time, a corrosion inhibitor to help protect metal components of the printer or ink delivery system, and a surfactant to adjust the ink surface tension. Various other components for use in an ink, such as colorant stabilizers, photoinitiators, binders, surfactants, electrolytic salts, pH adjusters, etc., may be employed as described in U.S. Pat. No. 5,681,380 to Nohr. et al. and U.S. Pat. No. 6,542,379 to Nohr, et al., which are incorporated herein in their entirety by reference thereto for all purposes.

When the thermochromic ink is applied to the skin of a patient (e.g., human or animal), it is normally desired that the thickness of the resulting coating is relatively small to enhance the detection sensitivity. For example, the thickness may range from about 0.01 millimeters to about 5 millimeters, in some embodiments, from about 0.01 millimeters to about 3 millimeters, and in some embodiments, from about 0.1 millimeters to about 2 millimeters. The desired thickness may be achieved by directly applying the thermochromic ink to the skin of a patient. Alternatively, the thermochromic ink may be initially applied to a substrate that is then used to transfer a thin coating onto the skin. The nature of the substrate may vary depending on the intended use, and may include materials such as films, paper, nonwoven webs, knitted fabrics, woven fabrics, foam, glass, etc. Desirably, the substrate is a wipe configured for use on skin, such as a baby wipe, adult wipe, hand wipe, face wipe, cosmetic wipe, household wipe, industrial wipe, personal cleansing wipe, cotton ball, cotton-tipped swab, and so forth.

The wipe may be formed from any of a variety of materials as is well known in the art. For example, the wipe may include a nonwoven web that contains an absorbent material of sufficient wet strength and absorbency for use in the desired application. For example, the nonwoven web may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19." Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other absorbent fibers that may be used in the present invention, such as abaca, sabai grass, milkweed floss, pineapple leaf, cellulosic esters, cellulosic ethers, cellulosic nitrates, cellulosic acetates, cellulosic acetate butyrates, ethyl cellulose, regenerated celluloses (e.g., viscose or rayon), and so forth.

Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al., which is incorporated herein in its entirety by reference thereto for all purposes.

If desired, the nonwoven web material may be a composite that contains a combination of synthetic thermoplastic polymer fibers and absorbent fibers, such as polypropylene and pulp fibers. The relative percentages of such fibers may vary over a wide range depending on the desired characteristics of the nonwoven composite. For example, the nonwoven composite may contain from about 1 wt. % to about 60 wt. %, in some embodiments from 5 wt. % to about 50 wt. %, and in some embodiments, from about 10 wt. % to about 40 wt. % synthetic polymeric fibers. The nonwoven composite may likewise contain from about 40 wt. % to about 99 wt. %, in some embodiments from 50 wt. % to about 95 wt. %, and in some embodiments from about 60 wt. % to about 90 wt. % absorbent fibers.

Nonwoven composites may be formed using a variety of known techniques. For example, the nonwoven composite may be a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes. Alternatively, the nonwoven composite may be formed be formed by hydraulically entangling fibers and/or filaments with high-pressure jet streams of water. Hydraulically entangled nonwoven composites of staple length fibers and continuous filaments are disclosed, for example, in U.S. Pat. No. 3,494,821 to Evans and U.S. Pat. No. 4,144,370 to Bouolton, which are incorporated herein in their entirety by reference thereto for all purposes. Hydraulically entangled nonwoven composites of a continuous filament nonwoven web and pulp fibers are disclosed, for example, in U.S. Pat. No. 5,284,703 to Everhart, et al. and U.S. Pat. No. 6,315,864 to Anderson, et al., which are incorporated herein in their entirety by reference thereto for all purposes.

Regardless of the materials or processes utilized to form the wipe, the basis weight of the wipe is typically from about 20 to about 200 grams per square meter (gsm), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al., which are incorporated herein in their entirety by reference thereto for all purposes.

The thermochromic ink may be applied to all or only a portion of the wipe or other substrate. Suitable techniques for applying the ink to the substrate include printing, dipping, spraying, melt extruding, coating (e.g., solvent coating, powder coating, brush coating, etc.), and so forth. In one embodiment, for example, the thermochromic ink is printed onto the support (e.g., wipe). A variety of printing techniques may be used for applying the thermochromic ink to the support, such as gravure printing, flexographic printing, screen printing, laser printing, thermal ribbon printing, piston printing, etc. In one particular embodiment, ink-jet printing techniques are employed to apply the ink to the support. Ink-jet printing is a non-contact printing technique that involves forcing an ink through a tiny nozzle (or a series of nozzles) to form droplets that are directed toward the support. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically. Thus, when the sample channel is formed from a dielectric material, DOD printing techniques may be more desirable.

If desired, the ink may also be applied to a strip that is subsequently adhered or otherwise attached to the substrate. For example, the strip may contain a facestock material commonly employed in the manufacture of labels, such as paper, polyester, polyethylene, polypropylene, polybutylene, polyamides, etc. An adhesive, such as a pressure-sensitive adhesive, heat-activated adhesive, hot melt adhesive, etc., may be employed on one or more surfaces of the facestock material to help adhere it to a surface of the substrate. Suitable examples of pressure-sensitive adhesives include, for instance, acrylic-based adhesives and elastomeric adhesives. In one embodiment, the pressure-sensitive adhesive is based on copolymers of acrylic acid esters (e.g., 2-ethyl hexyl acrylate) with polar co-monomers (e.g., acrylic acid). The adhesive may have a thickness in the range of from about 0.1 to about 2 mils (2.5 to 50 microns). A release liner may also be employed that contacts the adhesive prior to use. The release liner may contain any of a variety of materials known to those of skill in the art, such as a silicone-coated paper or film substrate.

The exact add-on level of the thermochromic ink on the substrate may vary based on a variety of factors, including the nature of the substrate, sensitivity of the color changing microcapsules, the presence of other additives, the desired degree of detectability (e.g., with an unaided eye), etc. In certain embodiments, for example, the substrate may be employed as a "wet wipe" in that it contains a significant portion of liquid, such as from about 150 to about 600 wt. % and in some cases, from about 300 to about 500 wt. % of the thermochromic ink based on the dry weight of the wipe.

Referring to FIG. 1, one embodiment of a method for obtaining a blood sample from the arm of a patient (or for infusing fluid into a patient) using the thermochromic ink of the present invention will now be described in more detail. Initially, a thermochromic ink 11 is disposed in contact with the skin 12 on an arm 13 of a patient. As discussed above, the temperature of the skin 12 in proximity to the vein 19 is generally greater than the temperature of the remaining portions of the skin 12. Thus, the skin 12 has a temperature pattern including areas of higher temperature in proximity to the vein 19. When the thermochromic ink 11 is placed on the skin 12, the different surface temperatures of the skin 12, which characterize the temperature pattern, provide the thermochromic ink 11 with a color pattern corresponding to the temperature pattern. Thus, in this embodiment, a stripe 37 forms as the color pattern that provides an excellent indication of the location of the vein 19. If desired, an elastic strap 18 may also be tightly wound around the upper portion of the arm 13 to enlarge the vein 19 and thereby facilitate its identification. Having located the vein 19, a syringe 15 and associated needle 17 may be used as is known in the art to puncture a vein 19 in the arm 13 and withdraw a sample of the blood in the vein 19. For example, the needle 17 associated with the syringe 15 can be inserted into the arm 13 at a point, such as the point 38, preferably in close proximity to the stripe 37. Alternatively, a needle may be inserted into the vein of the patient to infuse fluid into the vein by invasive techniques.

It should be understood that the aforementioned components may be provided separately or in combination as a kit. For example, the thermochromic ink 11 may be provided together as a kit with the syringe 15 (including the associated needle 17), elastic strap 18, etc. Other components commonly used in invasive procedures, such as a sanitizing solution (e.g., alcohol) may also be included with the kit if desired. Further, a separate substrate (e.g., wipe), such as described above, may also be included with the kit to help spread the ink onto the venous area of the skin.

The color change of the thermochromic ink of the present invention is rapid and may be detected within a relatively short period of time. For example, a visual change in color may occur in about 30 seconds or less, in some embodiments about 15 seconds or less, and in some embodiments, about 5 seconds or less. Further, the visual color change may remain observable for a length of time sufficient to identify the vein, such as about 1 second or more, in some embodiments about 2 seconds or more, and in some embodiments, from about 3 seconds to about 1 minute. The extent of the color change, which may be determined either visually or using instrumentation (e.g., optical reader), is also generally sufficient to provide a "real-time" indication of the vein location for use in a medical procedure. This color change may, for example, be represented by a certain change in the absorbance reading as measured using a conventional test known as "CIELAB", which is discussed in *Pocket Guide to Digital Printing* by F. Cost, Delmar Publishers, Albany, N.Y. ISBN 0-8273-7592-1 at pages 144 and 145. This method defines three variables, L*, a*, and b*, which correspond to three characteristics of a perceived color based on the opponent theory of color perception. The three variables have the following meaning:

L*=Lightness (or luminosity), ranging from 0 to 100, where 0=dark and 100=light;

a*=Red/green axis, ranging approximately from −100 to 100; positive values are reddish and negative values are greenish; and b*=Yellow/blue axis, ranging approximately from −100 to 100; positive values are yellowish and negative values are bluish.

Because CIELAB color space is somewhat visually uniform, a single number may be calculated that represents the difference between two colors as perceived by a human. This difference is termed ΔE and calculated by taking the square root of the sum of the squares of the three differences (ΔL*, Δa*, and Δb*) between the two colors. In CIELAB color space, each ΔE unit is approximately equal to a "just noticeable" difference between two colors. CIELAB is therefore a good measure for an objective device-independent color specification system that may be used as a reference color space for the purpose of color management and expression of changes in color. Using this test, color intensities (L*, a*, and b*) may thus be measured using, for instance, a handheld spectrophotometer from Minolta Co. Ltd. of Osaka, Japan (Model # CM2600d). This instrument utilizes the D/8 geometry conforming to CIE No. 15, ISO 7724/1, ASTM E1164 and JIS Z8722-1982 (diffused illumination/8-degree viewing system. The D65 light reflected by the specimen surface at an angle of 8 degrees to the normal of the surface is received by the specimen-measuring optical system. Typically, the color change that results in the venous area is represented by a ΔE of about 2 or more, in some embodiments about 3 or more, and in some embodiments, from about 5 to about 50.

The present invention may be better understood with reference to the following examples.

EXAMPLE 1

2 milliliters of a water-based magenta thermochromic ink (Chromicolor AQ-Ink, type#25 with a temperature transition of 31° C., Matsui International Co. Inc.) was placed on the top of a hand and spread thinly over the hand. The ink contained 49 wt. % thermosensitive microcapsules. Within a few seconds, the coating turned white, thereby showing veins as distinct lines while the rest of the coating remained magenta color. The coating was then applied to the forearm. Within seconds, clearly visible white lines of the veins were observed, while the rest of the coating remained magenta in color.

EXAMPLE 2

To 20 milliliters of a moisturizing hand antiseptic (62% ethanol, Kimberly-Clark Professional, San Antonio Tex.) was added 0.5 grams of red thermochromic powder (Color Change Corporation, Streamfield Ill., 31° C. temperature transition). The ink contained 20 wt. % thermosensitive microcapsules. The antiseptic and powder were then mixed to disperse the powder. 2 milliliters of the resulting solution was then placed onto the top of a hand and spread thinly with the use of a KimWipe™ tissue. Within seconds, the visible image of white lines showing where the veins were located appeared, while the rest of the coating remained red in color.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for identifying a vein in a patient, the method comprising:
    placing a thermochromic ink in direct contact with a venous area on the skin of a patient, wherein the thermochromic ink comprises thermosensitive color-changing microcapsules that contain a proton-accepting chromogen and a desensitizer, wherein the desensitizer possesses a melting point above which the chromogen is capable of becoming protonated, thereby resulting in a color change; and
    thereafter, observing the venous area for the color change.

2. The method of claim 1, wherein the proton-accepting chromogen is a leuco dye.

3. The method of claim 2, wherein the leuco dye includes a phthalide, phthalene, acyl-leucomethylene, fluorane, spiropyrane, cumarin, or a combination thereof.

4. The method of claim 1, wherein proton-accepting chromogens constitute from about 0.1 wt.% to about 20 wt.% of the microcapsules.

5. The method of claim 1, wherein the desensitizer has a boiling point of about 150° C. or higher.

6. The method of claim 1, wherein the desensitizer has a melting point of about from about 26° C. to about 34° C.

7. The method of claim 1, wherein the desensitizer includes a saturated or unsaturated alcohol, an ester of a saturated or unsaturated alcohol, an amide, or a combination thereof.

8. The method of claim 1, wherein desensitizers constitute from about 10 wt. % to about 70 wt. % of the microcapsules.

9. The method of claim 1, wherein the microcapsules further comprises a proton-donating agent.

10. The method of claim 9, wherein proton-donating agents constitute from about 0.5 wt. % to about 30 wt. % of the microcapsules.

11. The method of claim 1, wherein the microcapsules are formed from a polymer resin.

12. The method of claim 11, wherein polymer resins constitute from about 20 wt. % to about 80 wt. % of the microcapsules.

13. The method of claim 1, wherein the microcapsules having a mean particle size of from 10 nanometers to about 10 micrometers.

14. The method of claim 1, wherein the chromogen undergoes a color change at a temperature of from about 26° C. to about 34° C.

15. The method of claim 1, wherein the chromogen undergoes a color change at a temperature of from about 28° C. to about 33° C.

16. The method of claim 1, wherein the thermochromic ink further comprises a cooling agent.

17. The method of claim 16, wherein the cooling agent has an enthalpy of vaporization of about 40 kilojoules per mole or less.

18. The method of claim 16, wherein the cooling agent is an alcohol.

19. The method of claim 16, wherein cooling agents constitute from about 50 wt. % to about 99.9 wt. % of the ink and the microcapsules constitute from about 0.1 wt.% to about 50 wt. % of the ink.

20. The method of claim 16, wherein cooling agents constitute from about 30 wt. % to about 99 wt. % of the ink and the microcapsules constitute from about 1 wt. % to about 70 wt. % of the ink.

21. The method of claim 1, wherein the thermochromic ink is disposed on a substrate.

22. The method of claim 21, wherein the substrate contains a nonwoven web.

* * * * *